United States Patent [19]

Schwartz et al.

[11] 4,350,579
[45] Sep. 21, 1982

[54] TESTING APPARATUS FOR MEASURING IONS IN FLUIDS

[75] Inventors: Henry D. Schwartz, Palo Alto; Irwin H. Krull, Santa Clara; Carl J. Clement, Los Altos Hills; Frederick H. Stengel, Palo Alto; David D. Hayslett, San Jose, all of Calif.

[73] Assignee: Applied Medical Technology, Inc., Mountain View, Calif.

[21] Appl. No.: 183,983

[22] Filed: Sep. 4, 1980

[51] Int. Cl.³ .......................................... G01N 27/28
[52] U.S. Cl. .............................................. 204/195 R
[58] Field of Search ............... 204/195 R, 195 B, 1 T, 204/1 B, 1 A; 422/99, 68

[56] References Cited

U.S. PATENT DOCUMENTS

| | | | |
|---|---|---|---|
| 3,467,591 | 9/1969 | Frant | 204/195 R |
| 3,941,565 | 3/1976 | Schwartz | 23/230 B |
| 3,994,171 | 11/1976 | Schwartz | 73/423 A |
| 4,048,040 | 9/1977 | Schwartz | 204/195 R |

FOREIGN PATENT DOCUMENTS

| | | | |
|---|---|---|---|
| 493773 | 6/1953 | Canada | 422/68 |
| 678361 | 1/1964 | Canada | 422/99 |

Primary Examiner—G. L. Kaplan
Attorney, Agent, or Firm—Wolf, Greenfield & Sacks

[57] ABSTRACT

The testing apparatus is for measurement of ions in body fluids. The apparatus has a plurality of sample cups for containing fluids to be tested, a movable door for controlling access to the sample cups, and a plurality of measuring electrodes for immersion into the fluid to be tested. There is a hand operated device for moving the electrodes and the cups with respect to each other to alternately put the electrodes in a first position permitting access to the cups and in a second position in which the electrodes are immersed in the fluids to be tested contained in the cups. Means for mounting the cups in the testing apparatus are engaged with means for oscillating the cups independently of the electrodes. The oscillation fully exposes the electrodes to a representative sampling of the fluids within the cups and thus enhances the accuracy of the test being performed.

The method is for the measurement of chlorides, ionized calcium, sodium and potassium as well as other ions in fluids obtained from the body or elsewhere. The method includes the step of using the controlled oscillation of a small sample fluid in direct contact with an electrode, to thoroughly expose a true representative sample to the electrode for measurement.

35 Claims, 8 Drawing Figures

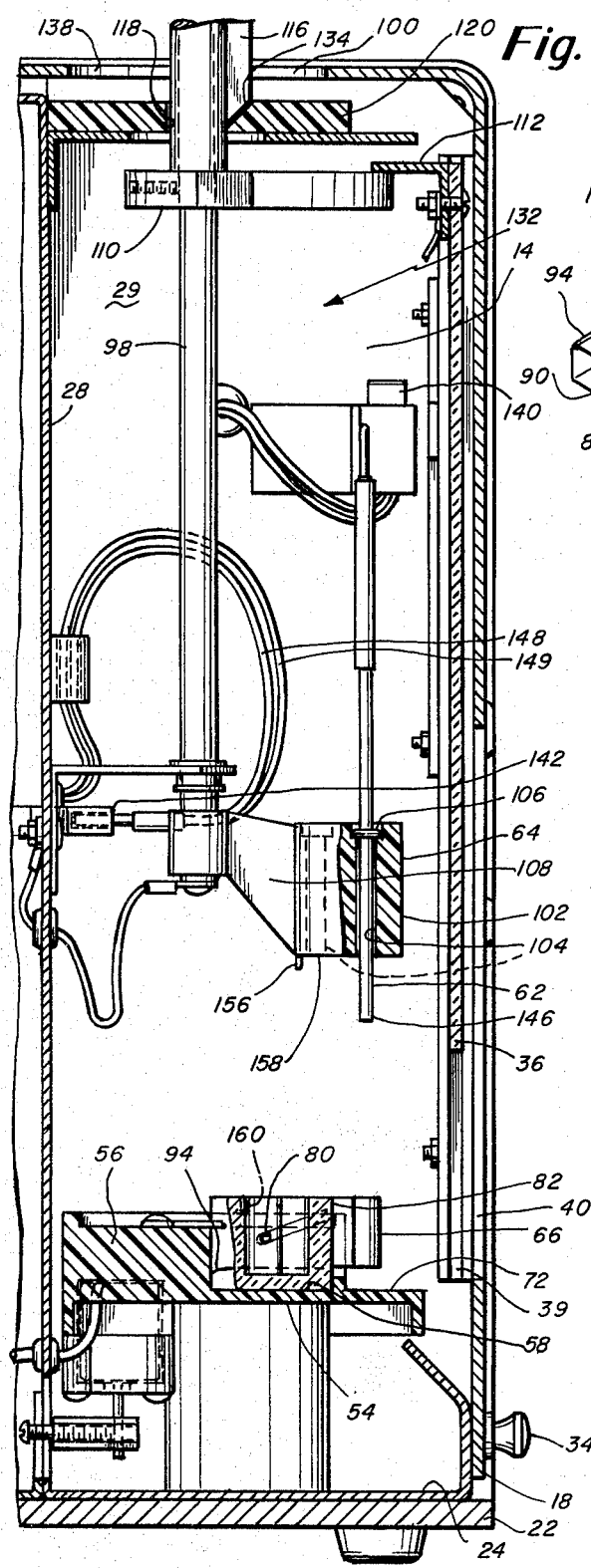
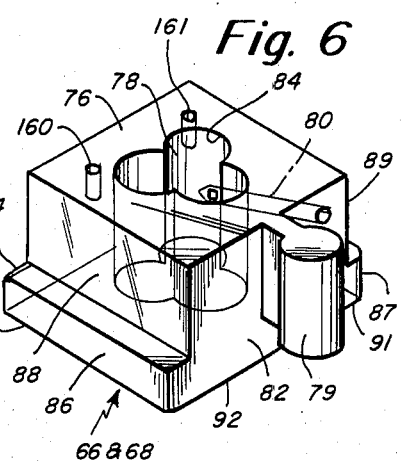

TESTING APPARATUS FOR MEASURING IONS IN FLUIDS

BACKGROUND OF THE INVENTION

The present invention generally relates to a testing apparatus for the measurement of ions in fluids to be tested. More particularly, this invention pertains to a clinical testing apparatus for measuring the concentrations and amounts of various ions in body fluids to be tested. U.S. Pat. Nos. 3,941,565; 3,994,171; and 4,048,040 describe certain prior test methods and apparatus of the present invention.

The importance of the electrolyte concentrations in body fluids is becoming apparent. Electrolytes have a complex role in regards to the control of the physiological balance of the body. Therefore, it is important that numerous ionic concentrations and levels in body fluids be quickly and easily ascertainable not only in a hospital setting but a doctor's office or small clinic.

Often presently available testing apparatus have one or more of a number of drawbacks which were often accepted by their users. In brief, most of the presently available testing apparatus are of the flow-through type in which the sample to be tested is moved by some means past a sensor such as an electrode partly in order that the sensor be constantly washed with the sample thereby providing a more exact measurement. These devices are generally large and may contain very intricate and complex tubing systems connected with one or more pumps to move the fluid through the tubes. These devices in many instances require the formation of bubbles within the tubing to improve the mixing of the fluid to be tested around the sensor or electrode that is immersed or located within the tubing. The equipment is generally large, requires considerable maintenance, and in almost every instance, tests a diluted sample. Dilution of samples has the drawback of degrading the exactness of the reading or measurement being taken. There is at least one device presently available in which the flow-through principal is not used. In that device, a sample is conveyed to a spinning chamber having an electrode within it and the measurement is taken while the chamber is spinning. Then the chamber has to be washed out with a washing solution before the next test is taken. The sample used in this device is also a diluted sample. The devices that are presently available often have fixed electrodes and the sample is pumped through a sometimes complex tubing system to the electrode.

SUMMARY OF THE INVENTION

The present invention provides a testing apparatus which is simple to use, manually operated, compact, and relatively inexpensive to manufacture and maintain.

Accordingly, an important object of the present invention is to provide a testing apparatus and method which can readily handle undiulted samples of the fluid to be tested. The testing of undiluted samples increases the exactness of the measurement made on the fluid.

Another object of the present invention is to provide an improved means for mixing a sample to be tested.

Another object of the present invention is to provide a testing apparatus in which sampling cups hold the fluids to be tested.

Another object of the present invention is to provide a testing apparatus in which standard carrying ions of the kind to be tested can be prepackaged within standard sampling cups intended for use in the testing apparatus.

Another object of the present invention is to provide a testing apparatus having a manually operated mechanical means for immersing electrodes in a fluid to be tested in the sampling cups.

Another object of the present invention is to provide a testing apparatus that is lightweight, easy and inexpensive to assemble.

Another object of the present invention is to provide a testing apparatus which may be used to test a broad range of fluids for any number of materials subject to the user's choice of sensing electrodes and electronics to perform the required calculations.

Yet another object of the present invention is to provide a sample cup which may be easily filled without waste or mess thus conserving small quantity samples for testing.

According to the invention, a testing apparatus is provided for use in the measurement of ions in fluids such as body fluids. The apparatus is preferably portable and has an enclosing casing. The casing has an area closed to the atmosphere by a door although it is not necessarily hermetically sealed. A hand operated vertically and horizontally movable electrode holder extends into the casing. Oscillating means are operatively arranged with respect to the electrode holder and have a plurality of spaced positions for mounting of sample cups or containers through access provided by the door. The electrode holder acts to provide positioning of an electrode or plurality of electrodes in any one of a plurality of sample cups positioned on the oscillating means. The sample cups are removable and cooperate with a detent means maintaining the sample cups in operative position with respect to the electrode holder. Preferably the electrode holder is interlinked with door means so that vertical movement of the electrode holder can actuate movement of electrodes as well as changing the position of the door. Preferably the electrode holder moves vertically along a substantially vertical axis and is pivotable about that axis to different horizontally spaced locations overlying one of a selected sample cup.

According to the method of this invention an improvement is provided in a method for the measurement of concentration of ions in fluids taken from the body in which a plurality of sample cups are used with an electrode means dipped successively in each of the sample cups to electrically determine the ion concentration therein. The improvement comprises the step of vertically moving an electrode holder by manual actuation with respect to a first sample container to immerse the electrode in fluid carried within the container and reciprocating the moving to remove the electrode. Steps further comprise horizontally moving the electrode with respect to the first sample cup to align it with a second sample cup by manual manipulation and again vertically moving the electrode with respect to the second sample cup to enable measurement of ion concentration in a second fluid.

A container is provided for use in the testing apparatus of this invention which container has a base with a plurality of walls extending upwardly from the base and having inner facing surfaces with an open top. Detent means of the testing apparatus are associated with the base and cooperate to hold the container in proper position within the testing apparatus. Preferably the container has a plurality of sample chambers formed by the walls which extend upwardly from the base and one of the sampling chambers is filled with a sample of predetermined ion concentration acting as a standard. The chamber is preferably generally clover-shaped in top plan view.

It is a feature of this invention that the testing apparatus and method can be used for clinical testing of body fluids such as serum, sputum, urine and the like as well as an industrial testing as in the testing of effluents for pollution problems. The sample cups can form a pre-packaged unit containing a standard to enhance ease of use of the machine. Overall the apparatus is extremely simple to manufacture and use by relatively unskilled personnel in a wide variety of areas including doctor's offices and emergency vehicle locations.

BRIEF DESCRIPTION OF THE DRAWINGS

Numerous other objects, features and advantages of the invention should now become apparent upon a reading of the following detailed description taken in conjunction with the accompanying drawings, in which:

FIG. 4 is a partial cross-sectional view similar to FIG. 3 showing a part of the testing apparatus in raised position;

FIG. 6 is a perspective view of one embodiment of a sample cup;

DETAILED DESCRIPTION

Figure 1:
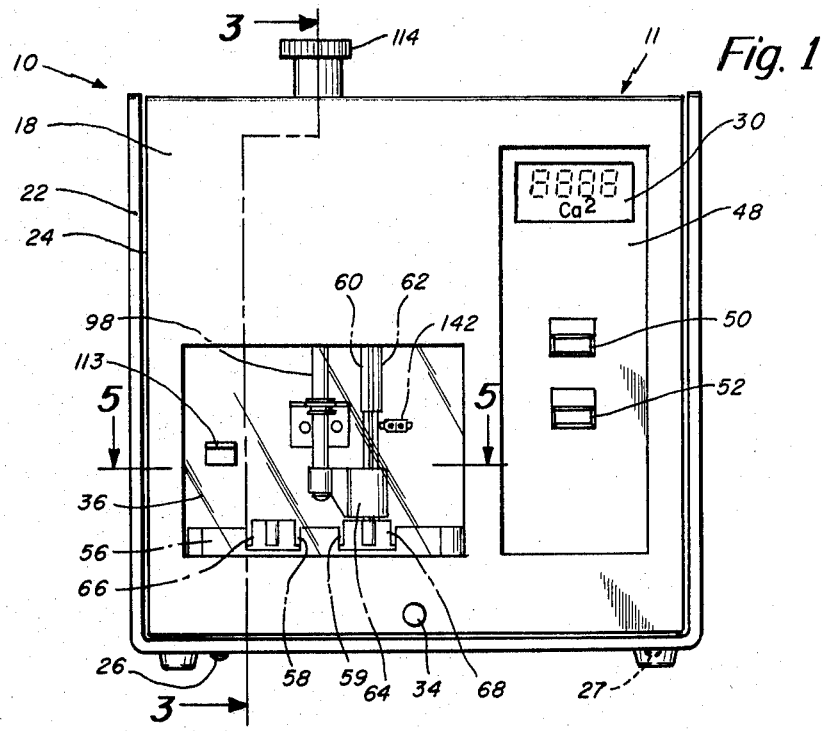
FIG. 1 is a front elevational view of a preferred embodiment of a testing apparatus.

A testing apparatus 10 as shown in FIGS. 1-5 for measuring the concentration of calcium ions in body fluids such as blood serum includes in its general organization a housing 11 having a rear cavity 12 and a forward cavity 14 and covers 16 and 18, respectively, for each of the cavities. The rear cavity contains a printed circuit board 20 which provides the necessary electronics. The front cavity contains a number of hand operated elements necessary to perform the desired tests on the fluids to be tested as is further described below.

The housing 10 includes a U-shaped member 22, and a casing 24 including the front cover 18 and the back cover 16. The casing fits within and is attached to the U-shaped member by fasteners 26, 27 located at the bottom of the casing. The U-shaped member forms the sides and bottom of the housing and the casing forms the front, back, and top of the housing. The front cavity 14 and rear cavity 12 are defined by interior walls 28 and 29. A digital readout display 20 is located on the front portion of the casing to one side of the front cavity. The front cover isolates the front cavity from the environment as well as providing access to the elements within the front cavity as is further described below. The front cover is pivotally attached to the casing by a piano hinge 32. The front cover may be secured in the closed position by lock mechanism 34 shown at the bottom of the cover in FIG. 3. An access door 36 is slidably attached to the front cover by vertical tracks 38, 39, thereby providing access to the front cavity through opening 40 even when the front cover is closed. The rear cavity is enclosed by back cover 16 which is pivotally connected to the casing by a second piano hinge 44. The back cover may be secured in the closed position by locking device 46. The casing incorporates in front wall 48 adjacent to the front cavity the digital readout display and two switches 50 and 52 that are utilized when calibrating the device.

The front cavity 14 contains the hand operated elements necessary to perform the desired tests on the fluids to be tested including an oscillating table 54, a block 56 incorporating detents 58, 59, a pair of electrodes 60, 62, an electrode holder 64, and a pair of sample cups 66 and 68. The oscillating table, isolated from the rest of the apparatus 10 by vibration isolators, 71, 73, is located in the bottom of the front cavity. The block incorporating the detents is attached to the top 72 of the oscillating table by a pair of threaded fasteners 74, 75. The fasteners are inserted through rubber shock mount vibration isolators 71, 73, to mount the block and thereby the detents in a precise position to a high tolerance on top of the oscillating table. One sample cup fits within each detent and is used to hold either a sample fluid to be tested, a high or a low standard fluid used for calibration of the testing apparatus, or a cleaning solution which may be used to periodically clean the electrodes and to keep their sensing surfaces wet while the apparatus is not in use.

Figure 3:
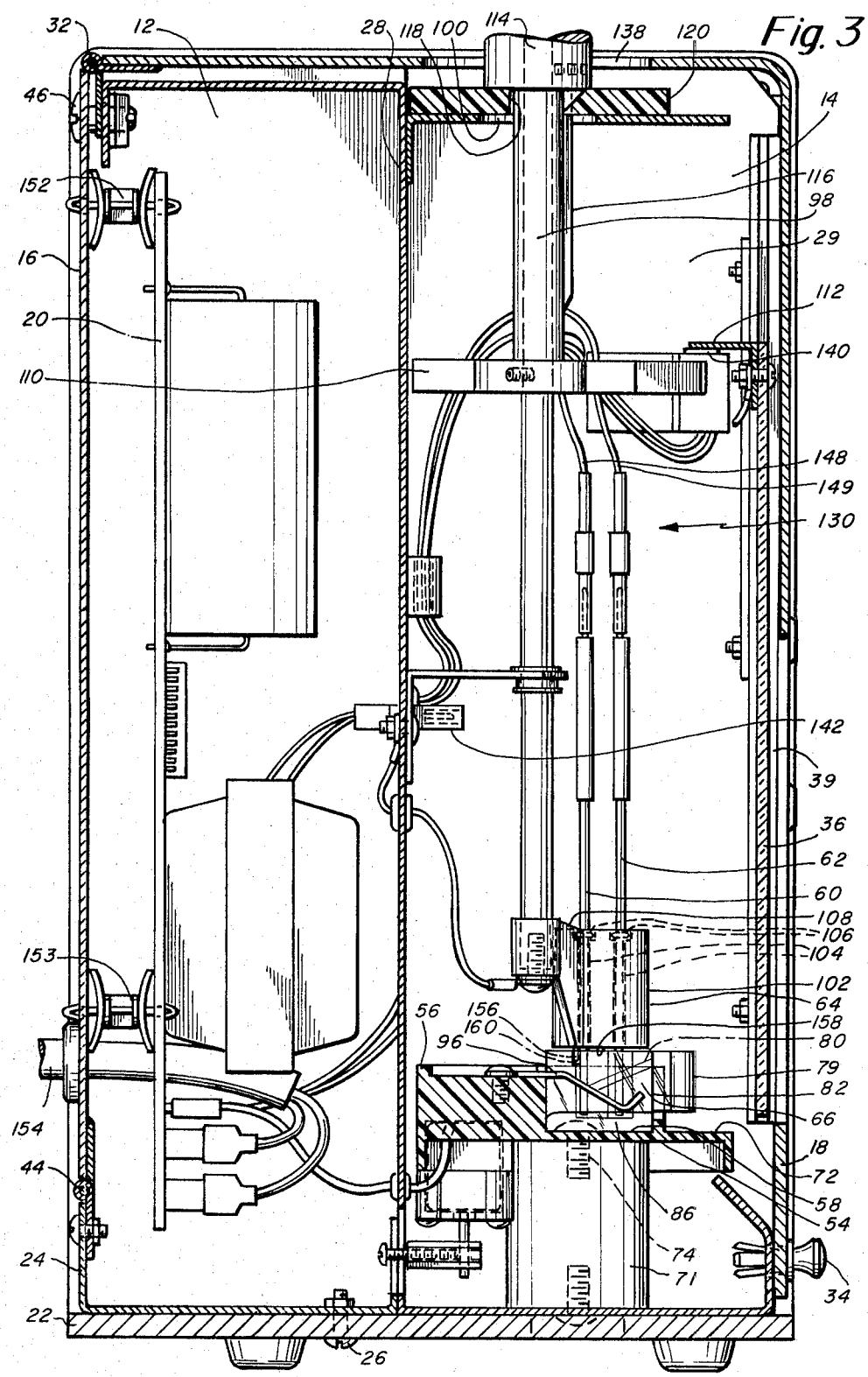
FIG. 3 is a full cross-sectional view taken along line 3—3 of FIG. 1.
Figure 5:
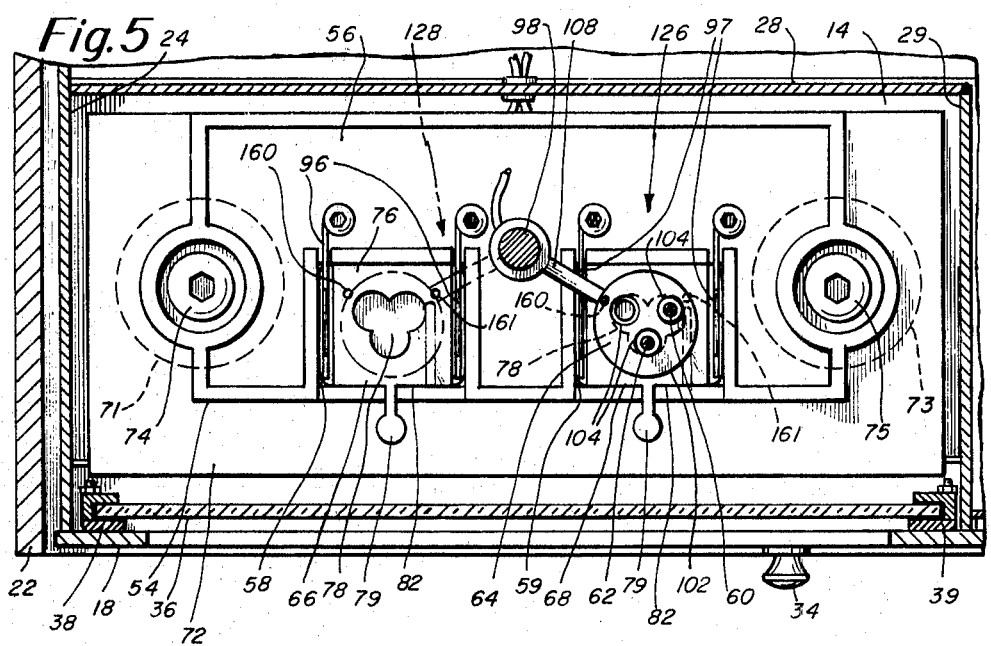
FIG. 5 is a cross-sectional view taken along line 5—5 of FIG. 1.

Each sample cup 66 and 68, as shown in FIG. 6, is a generally rectangular block 76 into which a sample chamber 78 has been milled to resemble the shape of 3 intersecting cylinders or a three-leafed clover when viewed in plan. Each sample cup is provided with a handle 79, as shown in FIG. 6, enabling the sample cup to be easily held and moved in and out of its associated detent on block 56. A passage 80 for injecting the desired fluid into the sample chamber passes through each block. The passage opens on front face 82 of the block. The longitudinal axis of the passage is tangent to the edge of a lobe 84 of the sample chamber allowing the sample fluids, standards, or cleaners to be injected into the sample chamber without having to be put in through the top of the sample cup. Each sample cup has a pair of flanges 86, 87 located on either side 88, 89 at the bottom of the block. The bottom surfaces 90, 91 are flush with the bottom 92 of the block. The rear portion 94 of the top surfaces of each flange is slightly beveled in order to engage a pair of springs 96, 97 attached to block 56, one pair on each side of each detent 58, 59. The springs are shown in FIGS. 3-5. The springs hold the sample cups in their respective detents by bearing down on the upper surfaces of the flanges thereby locking the sample cup firmly and precisely into place. It is anticipated that other locking mechanisms may be utilized to firmly and precisely hold the sample cups in place block 56.

Within the front cavity 14 and passing up through the top of casing 24 and the front cover 18 is a manually operated shaft 98 which is used to vertically raise and horizontally move the electrodes 60, 62 up and out of one sample chamber and move them over to and into the sample chamber on the adjacent sample cup. In a preferred embodiment, the shaft, slidably and rotably associated with opening 100 in the top of the casing over the cavity, has at its bottom the electrode holder 64 which securely holds the two electrodes in place when received by the sample chamber of either sample cup. The holder consists of a cylinder 102 having three holes 104 into which the electrodes may be placed. The longitudinal axes of the holes are not parallel and in fact define an imaginary cone that has its vertex located below the holder. Each electrode has an O-ring 106 around its circumference which acts to hold the electrode firmly in place within its respective hole in the electrode holder. The holder is attached to connecting web 108 which is in turn attached to the bottom of the shaft as shown in FIGS. 3, 4. The electrode is of the ion-selective type and may be either the solid state or the liquid filled type. The electrode of the present embodiment is calcium ion selective.

A little more than midway up the shaft 98 is horizontal lug 110 which engages an inner facing lip 112 attached to the top of the access door 36 so that when the shaft is vertically raised and lowered, the sliding door is also raised and lowered, thereby providing access to the sample cups. Since the lug operatively engages the lower surface of the lip the door may also be raised separately from the shaft by means of handle 113 on the outside of the door. An handwheel 114 located at the top of the shaft gives the testing apparatus user a good grip on the shaft and enables the user to easily pivot the shaft.

Figure 2:
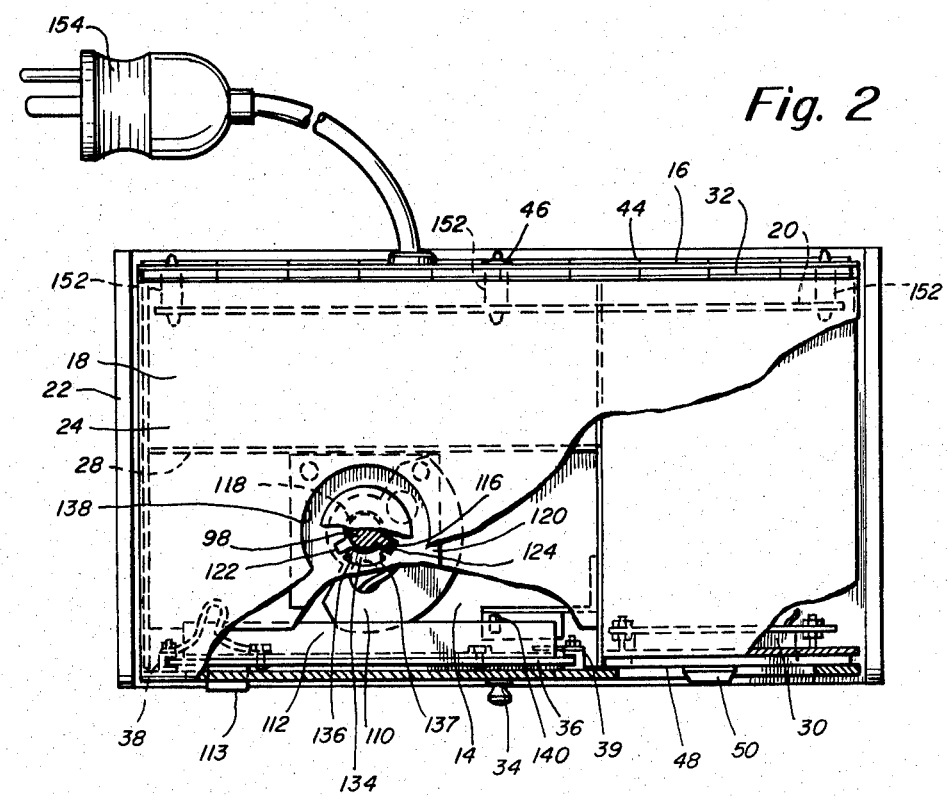
FIG. 2 is a top plan view of the testing apparatus partially cutaway to show its interior.

Key 116, shown in FIGS. 2-4 is located on the shaft 98 between the lug 110 and the handwheel 114. Opening 118 in the center of plate 120 attached to the top of the casing has two keyways 122 and 124 which extend radially out from the opening and are spaced about 120° apart. Openings 118 and 100 are in axial alignment. The key may be made to engage either one or the other of the keys thereby guiding the shaft in either a first horizontal position 126 or a second horizontal position 128. In a first vertical position 130, the shaft is fully within the front cavity and the electrodes will be in operative association with a sample chamber of either sample cup. In a second vertical position 132, the shaft is fully raised and may be brought into operative association with detent 134 at the top of the casing. At this point the shaft can only be pivoted between arcuately displaced detent limits 136, 137 and the detent at the top of the casing provides a rest for the shaft so that in a position intermediate the keyways the shaft is in a raised position and may be pivoted in an arc within the detent and between the keyways. The opening 138 in front cover 18 provides sufficient clearance for the front cover to be opened without interfering with the shaft and handwheel.

As shown in FIGS. 3-5, rods 156 (only one shown) depend from bottom surface 158 of cylinder 102 and register with holes 160, 161 in each sample cup when the electrodes are in operative association therewith. Should for some reason there be some misalignment of the cylinder the rods and holes will not properly register and the electrodes will be kept out of possibly damaging contact with the associated sample cup.

The cavity contains a microswitch 140 and a test jack 142, shown in FIGS. 3, 4. The microswitch is attached at one side of the front cavity 14 to interior wall 29 so that the lip 112 on the access door 36 engages the microswitch when the door is closed. The activated microswitch operates the oscillating table for approximately 10 (ten) seconds to sufficiently agitate and fully expose the sensing end 146 of the electrode to a representative sampling of a fluid within the sample chamber to thereby enhance the accuracy of the test being performed. Leads 148, 149 go to the electrodes from the printed circuit board 20 in the rear cavity 12. The leads may be removed from the top of the electrodes and placed into appropriate openings in jack 142 on back wall 28 of the front cavity as shown in FIG. 4 thereby performing a continuity check of the apparatus electronics.

Adjacent to the front cavity 14 and located at the front of the casing, as previously mentioned, is digital readout display 30 and two switches 50 and 52 used during calibration of the apparatus. The digital readout display consists of a light-emitting diode display which provides a reading of measurements taken by the electrodes and processed by the electronics on the printed circuit board 20. The top switch 50 is used for high standard calibration and the bottom switch 52 is used for low standard calibration, the use of which will be further described below. The printed circuit board is attached to the back cover by a number of plastic clips 152, 153 which allow the printed circuit board to be easily detached from the back cover and rotated to expose both sides for inspection, repair, or replacement of components. The housing, casing, and access door are connected to ground through a high quality capacitor (not shown) so that, although they are not grounded in the normal sense, electrical interference is effectively reduced or eliminated. Power cord and plug 154 are provided to supply power from a switchable electrical outlet to the testing apparatus. The digital readout mechanism and electronics can be any of the known prior art designs.

In the operation of clinical measurements of ionic concentrations in body fluids to be tested the operator obtains a quantity of a standard solution and a quantity of body fluid to be tested. The operation described hereinbelow represents the use of the testing apparatus of the present invention in which a measurement of the concentration of calcium ions in the body fluid is obtained.

In one embodiment, concentration of calcium ions with a 2+ valance in a body fluid is sought as an indicator vital to cardiac or critical care patients particularly for the proper management of renal, endocrine, and metabolic disorders. The operator obtains 250 microliters of a high standard and 250 microliters of a low standard solution and 250 microliters of the body fluid to be tested.

Preparing the apparatus to perform the desired test calls for the operator to fill the proper sample chambers and calibrate the apparatus as further described below. One of the sample chambers receives the low standard solution and the other receives the high standard solution. The operator fills the sample chambers after having vertically raised the shaft and placed key 116 in detent 134 which in turn has raised access door 36. The fluids are preferably placed in the sample chambers through the respective passages 80. This may be accomplished by inserting a hypodermic (not shown) filled with the proper fluid into the passage and depressing the plunger. In this way, the sample chambers may be filled without mess or waste which is particularly important when only a small amount of body fluid or sample fluid is available.

The operator now calibrates the testing apparatus. The operator pivots the shaft out of detent 134 so that key 116 engages keyway 124 thereby placing the electrode receptacle and electrodes over the sample cup containing the 250 microliters of low standard solution. Next by vertically lowering the shaft, the operator immerses the sensing portion of the electrodes into the standard solution and at the same time lip 112 on access door 36 operatively engages microswitch 140 energizing the oscillating table thereby agitating the standard solution. Within 10 (ten) seconds, the table stops and about 25 seconds later, the digital readout display becomes stable, switch 52 is depressed, and a reading is taken. The shaft is vertically raised and pivoted to horizontally move the electrodes over the sample cup containing the high standard solution. The test procedure is repeated as hereinbefore described except that switch 50 is depressed. If these readings do not become stable or agree with the known calibration values then the shaft should be vertically raised and the key placed in detent 134, the sample cups containing and standard solutions removed, the sample chambers cleaned, a new 250 microliters of standard solutions inserted in the sample chambers as hereinbefore described, and the calibration procedure repeated until the displayed value agrees with the known calibration values. When a suitable reading is obtained then the operator is ready to perform the first test. All the readings and digital readout displays result from calculations performed and signals generated by the circuits and components on the printed circuit board. There are a number of electronic circuits presently available and, therefore, mentioned only generally in the detailed description of the present invention. It should be noted that the above-described calibration procedure need not be performed before every test but only periodically as the test and apparatus conditions warrant.

Following calibration of the apparatus, the operator performs the desired test as described below. After the calibration has been performed the operator vertically raises the shaft by handwheel 114 and rests key 116 in detect 134. The operator injects 250 microliters of low standard into the sample chamber of sample cup 68 and 250 microliters of the body fluid to be tested into the sample chamber of sample cup 66. The outside of the access door may be marked with the terms STANDARD and SAMPLE in front of the sample cups to minimize confusion particularly when a large number of tests have to be performed or repeated. The shaft is pivoted to engage key 116 with keyway 124 and the shaft is vertically lowered thereby immersing the sensing portion of the electrodes into the low standard. As before, vertically lowering the shaft lowers the access door and the lip 112 engages microswitch 140, as shown in FIG. 3, to energize the oscillating table which continues to oscillate for approximately 10 (ten) seconds. The operator pauses for about 25 seconds and then depresses switch 52. If the display does not indicate a stable reading then a new 250 microliter low standard should be used and the above portion of the test procedure is repeated. If the display flashes then the calibration procedure was improperly performed and the calibration should be carefully repeated. Assuming the calibration was properly performed, then the operator notes the standard value displayed and then vertically raised the shaft, pivots it vertically lowers it thereby immersing the sensing portion of the electrodes into the body fluid to be tested. As previously described, vertically lowering the shaft energizes the oscillating table. Approximately 25 seconds after the oscillating table has stopped the concentration value displayed is noted by the operator. If more tests are to be performed the operator places a new cup in detent 58 and injects 250 microliters of the body fluid to be tested into this sample cup's sample chamber and repeats the test procedure as hereinbefore described.

In the preferred embodiment electrode continuity may be checked at any time by removing from the upper ends of the electrodes transmitting wires and then plugging the loose ends into jacks as hereinbefore described. The testing apparatus electronics generate a flashing or unstable display if the electrodes are faulty. Electrodes may be easily replaced simply by removing them from their respective holes in the receptacle, removing the leads from the defective electrode, connecting the wires to a new electrode equipped with an O-ring, and inserting the new electrode into the proper hole in the electrode receptacle.

Figure 7:
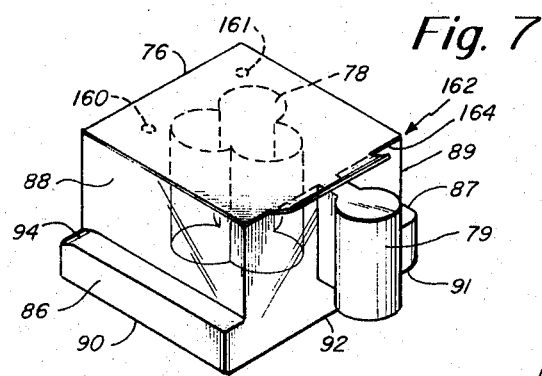
FIG. 7 is a perspective view of another embodiment of a sample cup.
Figure 8:
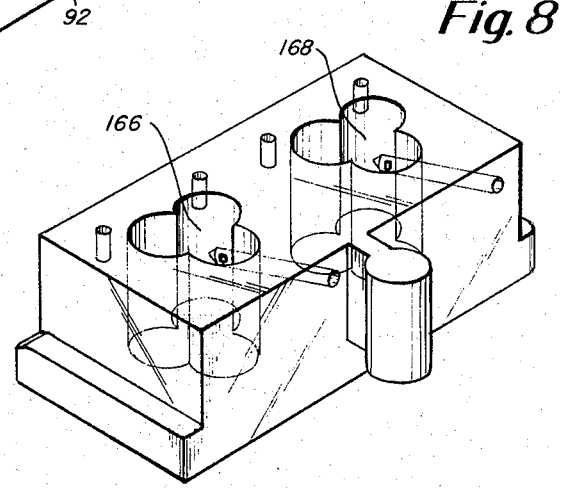
FIG. 8 is a perspective view of a two sample chamber sample cup.

Other sample cup embodiments may be used with the testing apparatus as shown in FIGS. 7, 8.

In FIG. 7, sample cup 162 includes in its structure parts 76, 78, 79, 86, 87, 88, 89, 90, 91, 92, 94, 160, and 161 corresponding to the same parts in the sample cup shown in FIG. 6. Identical parts in both parts are given the same number with foil seal 164 added. Foil seal 164 differentiates sample cup 162 from those previously described. The foil seal provides means to store pre-measured portions of standard fluids allowing the testing apparatus operator to quickly and easily prepare a pre-measured quantity of a fresh standard solution thereby increasing the speed and accuracy of the post-calibration tests.

In FIG. 8 is shown an embodiment in which sample cups have been integrated into a single structure. One or both of the sample chambers 166, 168 may be sealed with a foil seal as shown in FIG. 7.

While specific embodiments have been shown and described, many variations are possible. The particular electronics used as well as the door opening, raising, lowering sequences can be changed as desired. In all cases manual actuation of the sample holder with respect to the electrodes is preferred in order to maintain a simplified device readily available for use in the field as well as in factory and laboratory situations. The sample container configuration can vary greatly as can its materials, although light-weight plastics which can be throwaway items are preferred. The configuration of the sample chambers can vary although the clover-leaf design is preferred. Similarly, sizes and dimensions can change considerably although in the preferred embodiment, the device can be dimensioned so as to fit entirely within a cube having dimensions of $1''\times 1''\times 1''$.

What is claimed is:

1. A testing apparatus for use in the measurement of ions in fluids to be tested, the testing apparatus comprising:
   a plurality of sample cups, each cup defining a sampling chamber for containing a fluid to be tested,
   a movable door which controls access to the sample cups,
   a plurality of measuring electrodes mounted for movement from a first generally vertical position spaced from one of the sample cups, and a second generally vertical position in operative engagement with a chamber of the cup whereby the electrodes in the second vertical position are immersed in a sample fluid carried within the chamber,
   means for moving the electrodes and cups with respect to each other into the first and second vertical positions respectively, the means for movement comprising a mechanical means and carrying detent means for locking the electrodes in any one of a plurality of horizontally positioned locations and permitting access to one of the cups in the first generally vertical position, means for mounting cups in predetermined substantially horizontally spaced loci corresponding to horizontal detent positions of the means for moving the electrodes, the means for mounting the cups being engaged with a means for oscillating, the oscillating means being interlinked with the cup mounting means and independent of the electrodes, the oscillating means providing oscillated positions of the cups, each of which is spaced from the electrodes at all times and at all positions of the electrodes, the oscillating means being constructed and arranged to oscillate fluid within the chambers over surfaces of the electrodes when the electrodes are in the second vertical position in one of the cups in order to fully expose the electrodes to a representative sampling of the fluids within the chamber of the last mentioned cup and thus enhance the accuracy of the test being performed.

2. A testing apparatus in accordance with claim 1 further comprising means for engaging and releasing the door to move the door simultaneously with the electrodes into a position permitting access to the sample cups when the electrodes are in the first vertical position and a position closing access to the sample cups and protecting the cups from the environment when the electrodes are in the second vertical position.

3. A testing apparatus in accordance with claim 1 wherein the cups are incorporated into a single integral structure.

4. A testing apparatus in accordance with claim 3 wherein said single integral structure comprises a base,
a plurality of walls extending upwardly from the base defining inner facing surfaces,
means associated with the base cooperating with detent means within testing apparatus whereby the container is held in a proper position within the testing apparatus,
the inner facing surfaces of the outwardly extending walls defining a sampling chamber.

5. A testing apparatus in accordance with claim 1 further comprising means for calculating the desired ion measurement in operative association with the electrodes.

6. A testing apparatus in accordance with claim 5 further comprising means for displaying the value of the ion measurement.

7. A testing apparatus in accordance with claim 6 wherein the display means is a light emitting diode display.

8. A testing apparatus in accordance with claim 1 further comprising a switch activating the means for oscillating.

9. A testing apparatus in accordance with claim 8 wherein the switch is in operative association with the movable door when the door is closed.

10. A testing apparatus in accordance with claim 1 further comprising a timing means to stop the means for oscillating after a predetermined interval of oscillating.

11. A testing apparatus in accordance with claim 1 wherein the means for oscillating acts to oscillate in a single plane.

12. A testing apparatus in accordance with claim 1 wherein the means for oscillating acts to oscillate at a frequency between 100 and 500 hertz.

13. A testing apparatus in accordance with claim 1 wherein the means for oscillating is an oscillating table.

14. A testing apparatus in accordance with claim 1 further comprising means for calibrating the testing apparatus.

15. A testing apparatus for use in the clinical measurement of ions in body fluids to be tested, the testing apparatus comprising:

a first sample cup and a second sample cup, each cup defining a sampling chamber for containing a fluid to be tested, a movable door for controlling access to the sample cups and mounted for movement to an open and closed position, a plurality of measuring electrodes mounted for movement from a first position spaced from the sample cups and a second position in operative engagement with a chamber of one of the cups, whereby the electrodes in the second position are immersed in fluid carried within the chamber, means for moving the electrodes and cups with respect to each other into the first and second positions, the means for movement comprising a mechanical means and carrying detent means for locking the electrodes in first and second horizontally positioned locations to permit access to one or the other of the cups, means for mounting the cups in predetermined substantially horizontally spaced loci corresponding to the first and second horizontal detent positions of the means for moving the electrodes, the means for mounting the cups being engaged with a means for oscillating being interlinked with the cup mounting means and independent of the electrodes, the oscillating means providing oscillated positions of the cups, each of which is spaced from the electrodes at all times and at all positions of the electrodes, the oscillating means being constructed and arranged to oscillate the fluid within the chamber over surfaces of the electrodes when the electrodes are in the second position in order to fully expose the electrodes to a representative sampling of the fluids within the cup and thus enhance the accuracy of the test being performed.

16. A testing apparatus in accordance with claim 15 further comprising means for engaging and releasing the door to move the door simultaneously with the electrodes into a position permitting access to the sample cups when the electrodes are in the first position and a position closing access to the sample cups and protecting the cups from the environment when the electrodes are in the second position.

17. A testing apparatus in accordance with claim 15 wherein the sample cups are incorporated into a single integral structure.

18. A testing apparatus in accordance with claim 15 further comprising means for calculating the ion measurement in operative association with the electrodes.

19. A testing apparatus in accordance with claim 15 further comprising a means for displaying the ion measurement.

20. A testing apparatus in accordance with claim 19 wherein the display means is a light emitting diode display.

21. A testing apparatus in accordance with claim 15 further comprising a switch to activate the means for oscillating.

22. A testing apparatus in accordance with claim 21 wherein the switch is in operative association with the movable door when the door is closed.

23. A testing apparatus in accordance with claim 15 further comprising a timing means operatively controlling the means for oscillating whereby the oscillation of the sample cups is stopped after a predetermined interval of oscillation.

24. A testing apparatus in accordance with claim 15 wherein the means for oscillating act to oscillate in a single plane.

25. A testing apparatus in accordance with claim 15 wherein the means for oscillating act to oscillate at a frequency between 100 and 500 hertz.

26. A testing apparatus in accordance with claim 15 wherein the means for oscillating is an oscillating table.

27. A portable testing apparatus for use in the measurement of ions in fluids,
said apparatus having an enclosing casing,
said enclosing casing including an area closed to the atmosphere by door means,
a hand operable vertical and horizontally movable electrode holder,
oscillating means operatively arranged with respect to said electrode holder and having a plurality of spaced positions for mounting of sample chambers through access provided by said door means,
said electrode holder acting to provide positioning of an electrode in any one of a plurality of sample chambers positioned on said oscillating means,
said sample chambers being removable and cooperating with a detent means for maintaining said sample chambers in operative position with respect to said electrode holder.

28. A testing apparatus in accordance with claim 27 and further comprising said electrode holder being interlinked with said door means so that vertical movement of said electrode holder can actuate movement of electrodes mounted therein as well as changing the position of said door means.

29. A testing apparatus in accordance with claim 28 and further comprising holder being mounted for reciprocal vertical movement along an axis to horizontally position an electrode.

30. A testing apparatus in accordance with claim 29 and further comprising said sample chambers being two in number.

31. A testing apparatus in accordance with claim 29 and further comprising said sample chambers being two in number and integrally formed as a unit with one of said sample chambers carrying a sealed predetermined standard for the ions to be tested in the apparatus.

32. A portable testing apparatus in accordance with claim 27 wherein said sample chambers are contained in two separate containers of plastic.

33. A portable testing apparatus in accordance with claim 32 wherein one of said containers has a removable sealing cover.

34. A portable testing apparatus in accordance with claim 27 wherein said sample chambers are contained in a single plastic block.

35. A portable testing apparatus in accordance with claim 34 and further comprising said plastic block comprising a base, a plurality of walls extending upwardly from the base defining inner facing surfaces, detent means for cooperating with detent means of said apparatus to hold said plastic block on said oscillating means.

* * * * *